(12) United States Patent
Paillet

(10) Patent No.: US 11,857,439 B2
(45) Date of Patent: Jan. 2, 2024

(54) METHOD FOR MANUFACTURING A CUSTOMIZED SLEEVE FOR A PROSTHESIS

(71) Applicant: Stéphane Paillet, Visan (FR)

(72) Inventor: Stéphane Paillet, Visan (FR)

( * ) Notice: Subject to any disclaimer, the term of this patent is extended or adjusted under 35 U.S.C. 154(b) by 739 days.

(21) Appl. No.: 17/041,380

(22) PCT Filed: Mar. 21, 2019

(86) PCT No.: PCT/FR2019/050646
§ 371 (c)(1),
(2) Date: Sep. 24, 2020

(87) PCT Pub. No.: WO2019/186033
PCT Pub. Date: Oct. 3, 2019

(65) Prior Publication Data
US 2021/0030567 A1    Feb. 4, 2021

(30) Foreign Application Priority Data
Mar. 26, 2018    (FR) ...................... 1852594

(51) Int. Cl.
| | | |
|---|---|---|
| *A61F 2/00* | (2006.01) | |
| *B29C 45/00* | (2006.01) | |
| *B29C 65/00* | (2006.01) | |
| *A61F 2/50* | (2006.01) | |
| *B29C 45/14* | (2006.01) | |
| *B29C 65/48* | (2006.01) | |
| *A61F 2/78* | (2006.01) | |
| *B29K 83/00* | (2006.01) | |
| *B29K 105/00* | (2006.01) | |
| *B29L 31/00* | (2006.01) | |

(52) U.S. Cl.
CPC ........ *A61F 2/5046* (2013.01); *B29C 45/0053* (2013.01); *B29C 45/14065* (2013.01); *B29C 45/14336* (2013.01); *B29C 65/48* (2013.01); *B29C 66/729* (2013.01); *A61F 2002/5053* (2013.01); *A61F 2002/5056* (2013.01); *A61F 2002/7837* (2013.01); *B29C 2045/0079* (2013.01); *B29C 2045/14155* (2013.01); *B29K 2083/00* (2013.01); *B29K 2105/0061* (2013.01); *B29L 2031/7532* (2013.01)

(58) Field of Classification Search
CPC .... A61F 2/00; A61F 2/50; A61F 2/504; A61F 2/5046; B29C 45/00; B29C 45/005; B29C 45/0053; B29C 45/10; B29C 45/14; B29C 45/1406; B29C 45/14065; B29C 45/143; B29C 45/1433; B29C 45/14336; B29C 65/00; B29C 65/40; B29C 65/48; B29C 66/00; B29C 66/70; B29C 66/72; B29C 66/729

See application file for complete search history.

(56) References Cited

U.S. PATENT DOCUMENTS

| | | | |
|---|---|---|---|
| 5,728,368 A | 3/1998 | Bou et al. | |
| 2003/0181989 A1* | 9/2003 | Eberle | ................... A61F 2/7812 623/36 |
| 2008/0234836 A1* | 9/2008 | Taylor | ................... B29C 70/446 623/33 |
| 2015/0079014 A1* | 3/2015 | Ingvarsson | ........... A61L 27/306 424/68 |

FOREIGN PATENT DOCUMENTS

| | | |
|---|---|---|
| EP | 0976371 A1 | 2/2000 |
| FR | 2799953 B1 | 7/2002 |
| FR | 2994079 A1 | 7/2014 |

OTHER PUBLICATIONS

International Search Report for International Application No. PCT/FR2019/050646 dated Jun. 3, 2019, 2 pages.
International Written Opinion for International Application No. PCT/FR2019/050646 dated Jun. 3, 2019, 6 pages.

\* cited by examiner

*Primary Examiner* — Jacob T Minskey
*Assistant Examiner* — Matthew Hoover
(74) *Attorney, Agent, or Firm* — TraskBritt

(57) ABSTRACT

A method for manufacturing a customized sleeve for a prosthesis, comprises the following steps: (a) providing a mold of an end of a limb of an individual who is intended to receive said prosthesis; (b) providing a preform made of an elastomer material, said preform comprising an open proximal end and a closed distal end; (c) positioning said preform on the mold; (d) positioning on said preform at least one element from: a polymer reinforcement, a layer of an elongation-preventing fabric, a distal cup and an air discharge sheath; (e) positioning a vacuum cover around the preform; (f) creating a vacuum and injecting a polymer cross-linkable at room temperature into said vacuum cover so as to form a coating having a uniform thickness over the preform and each element which is positioned on said preform.

12 Claims, 5 Drawing Sheets

METHOD FOR MANUFACTURING A CUSTOMIZED SLEEVE FOR A PROSTHESIS

CROSS-REFERENCE TO RELATED APPLICATIONS

This application is a national phase entry under 35 U.S.C. § 371 of International Patent Application PCT/FR2019/050646, filed Mar. 21, 2019, designating the United States of America and published as International Patent Publication WO 2019/186033 A1 on Oct. 3, 2019, which claims the benefit under Article 8 of the Patent Cooperation Treaty to French Patent Application Serial No. 1852594, filed Mar. 26, 2018.

TECHNICAL FIELD

The present disclosure relates to a method for manufacturing a customized sleeve for a prosthesis, and to a sleeve obtained using the method.

BACKGROUND

When an individual having undergone an amputation of an end of a limb must be fitted with a prosthesis, a sleeve is usually placed between the stump and the prosthesis. The sleeve serves as a cutaneous interface between the prosthesis and the limb, designed to improve the grip of the prosthesis on the skin and to improve the comfort of the individual.

The sleeve must be specially adapted to the size and shape of the individual's limb.

A first possibility is to select, from among a range of existing sleeves of different sizes, the one most suited to the individual, based on measurements taken from the individual.

However, it is rare, often difficult, to be able to find among these standard sleeves a sleeve that perfectly fits the individual.

To overcome this drawback, customized sleeves are manufactured, based on the dimensions taken from the individual or based on a mold of a limb to be fitted up.

In order to minimize the time and cost of making such a sleeve, some methods involve using a prefabricated preform, which may be available in several standard sizes from which the one most suited to the individual can be chosen, and shaping the preform in order to adapt it to the individual's limb.

Thus, for example, document FR 2 799 953 describes a method of manufacturing a sleeve comprising the supply of a thermoformable preform, specifically made of a polyolefin foam or ethylene vinyl acetate (EVA), heating the preform to soften it, then fitting the preform directly onto the stump of the individual or onto a mold defining the external shape of the stump.

Document FR 2 994 079 describes a method for manufacturing a sleeve comprising the supply of a thermoformable preform, specifically made of a styrene ethylene butylene styrene (SEBS) copolymer, created by plastic injection and of uniform thickness, positioning the preform on a mold defining a reduction of the stump, heating the preform/mold assembly and demolding after cooling.

However, these methods only make it possible to check the internal shape of the sleeve, which is defined by the external surface of the mold. Furthermore, these forming methods do not make it easy to incorporate the components into the sleeve. These components can, for example, be reinforcements, an elongation-preventing fabric, a cup arranged on the stump, etc. The incorporation of these components requires reworking operations, specifically gluing, on the stump after forming.

Another technique involves manufacturing a counter-mold, defining the external form of the sleeve, and injecting liquid silicone into the gap between this counter-mold and the mold, which forms a mold impression. After solidification, the silicone sleeve thus obtained is demolded. Reinforcements or an elongation-preventing fabric may be inserted into the impression before injecting the liquid silicone or during a second reinforcement injection. However, this method is relatively lengthy as it requires several prior operations to manufacture the counter-mold by thermoforming. Moreover, obtaining a uniform thickness relies heavily upon the skill of the technician; in fact, due to poor initial positioning of the counter-mold in relation to the mold, the thickness may be too thick in some areas of the sleeve and too thin in others. In this case, it may be necessary to carry out manual repairs to the sleeve after demolding.

BRIEF SUMMARY

One object of the present disclosure is to devise a more repeatable, faster and cheaper method for forming a customized prosthetic sleeve.

To this end, the present disclosure proposes a method for manufacturing a customized sleeve for a prosthesis, comprising the following steps:
 (a) providing a mold of an end of a limb of an individual who is intended to receive the prosthesis;
 (b) providing a preform made of an elastomer material, the preform comprising an open proximal end and a closed distal end;
 (c) positioning the preform on the mold;
 (d) positioning on the preform at least one element from: a polymer reinforcement, a layer of an elongation-preventing fabric, a distal cup and an air discharge sheath;
 (e) positioning a vacuum cover around the preform;
 (f) creating a vacuum and injecting a polymer cross-linkable at room temperature into the vacuum cover so as to form a coating having a uniform thickness over the preform and each element, which is positioned on the preform.

"Room temperature" in the present text means a temperature of between 20 and 25° C.

"Customized" in the present text means that the sleeve is specially adapted to the morphology of the individual.

According to one embodiment, the preform is a silicone gel.

According to one embodiment, the material injected around the preform is a bi-component silicone.

Advantageously, all of the steps can be performed at a temperature of between 20 and 25° C.

Preferably, the preform has a variable thickness. Advantageously, the preform has a greater thickness at its distal end than at its proximal end.

Advantageously, the method comprises, after cross-linking of the polymer injected around the preform, the gluing of a resilient fabric or the application of a slippery paint onto the external surface of the sleeve.

Other subject matter concerns a sleeve obtained by the method just described. The sleeve comprises:
 a preform made of an elastomeric material,
 at least one element chosen from: a polymer reinforcement, a layer of an elongation-preventing fabric, a distal cup and an air discharge sheath, a covering of a polymer cross-linkable at low temperature coating the preform and the element, the element having a uniform thickness.

BRIEF DESCRIPTION OF THE DRAWINGS

Further features and advantages of the present disclosure will emerge from the following detailed description, with reference to the accompanying drawings in which.

To make the figures easier to interpret, the different elements are not necessarily shown to scale.

DETAILED DESCRIPTION

The present disclosure makes it possible to achieve better repeatability of the quality of the sleeve, particularly in terms of thickness, thanks to the use of a preform of consistent quality, and to the injection of an even layer of a polymer cross-linkable at low temperature around the preform, so as to incorporate the different components of the sleeve.

Figure 1:
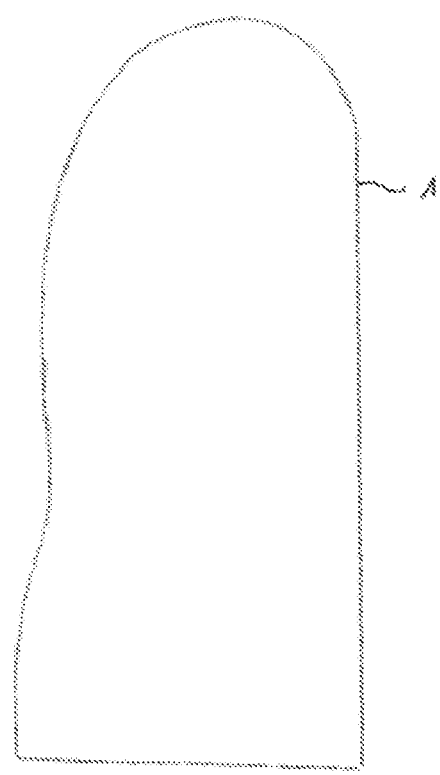
FIG. 1 is a side view of a mold of a limb to be fitted with the prosthesis.

FIG. 1 is a schematic representation of a mold 1 of the limb to be fitted up.

Advantageously, the mold is reduced in relation to the limb, by applying a reduction rate defined by the correction nomograms currently used in the field of prosthesis design. The application of this reduction allows the final sleeve to be fitted with a slight gripping on the limb, in order to ensure a good hold of the sleeve.

The mold can be manufactured using any known technique, for example, from a mold of the limb, or from a three-dimensional image of the limb.

The mold can be of resin, plaster, polyurethane foam or any other material suitable for the implementation of the method described below.

A preform made of an elastomeric material, such as a silicone gel, is provided.

The preform has an open proximal end (to fit onto the limb) and a closed distal end (to accommodate the stump). The internal surface of the preform is designed to be in contact with the skin when the prosthesis is being worn.

The polymer constituting the preform is chosen primarily for the comfort that it affords the individual, since it is in direct contact with the skin. A person skilled in the art is capable of choosing the appropriate hardness.

This preform is manufactured beforehand in one or more standard sizes. It is not therefore specific to the patient. However, if various preforms are available, the practitioner can choose the most appropriate based on the morphology of the patient. Usually, the preform has a slightly smaller circumference than that of the mold, so as to slightly grip thereon on assembly.

Advantageously, the preform has a non-uniform thickness specifically with areas of excess thickness to ensure improved comfort for the patient. The thickness is thus usually greater at the distal end of the preform and thinner at its proximal end.

According to a variation, the preform has a uniform thickness.

The preform is manufactured industrially using molding techniques that ensure an excellent repeatability of the thicknesses and, more generally, the quality of one preform to the next.

Figure 2:
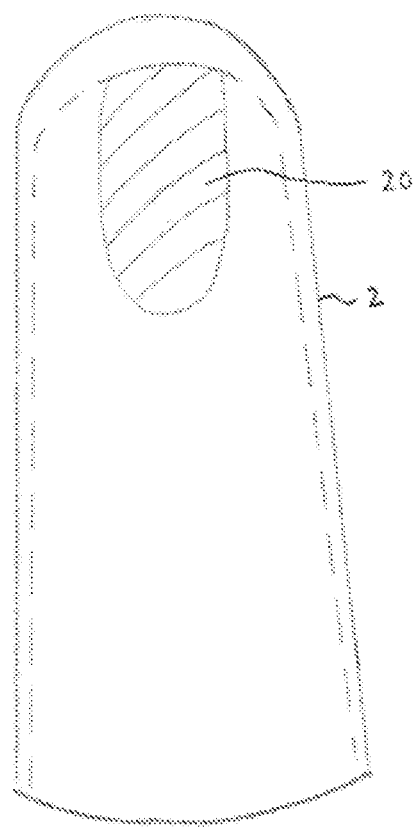
FIG. 2 is a view of the preform before it is positioned on the mold shown in FIG. 1.

FIG. 2 shows the preform 2 before it is positioned on the mold 1. In the example shown, the preform comprises a reinforcement 20 shown by cross-hatching, formed by an excess thickness extending in a longitudinal direction.

The practitioner then positions on the preform the various components intended to be integrated into the sleeve. These components may comprise:
- one of more reinforcements, which are generally in the form of polymer patches (silicone, for example);
- one or more layers of an elongation-preventing fabric, which is a fabric that can be stretched in one direction only, so that the elongation of the sleeve can be controlled;
- a cup intended to be positioned on the stump and consequently placed at the distal end of the preform, the cup possibly being provided with an element to secure the prosthesis (for example, a threaded end intended to retain the prosthesis by screwing);
- a sheath made, for example, of polyamide, having sufficiently large meshes to enable the discharge of the air contained between the preform and the sheath when creating the vacuum, which will be performed subsequently;
- possibly, a resilient fabric contributing to reinforce the sleeve and/or improve its appearance.

Once this assembly has been completed, a vacuum cover is positioned around the preform. In a known way, the vacuum cover is made of an airtight material and allows a vacuum to be created around the preform, before the injection of a polymer cross-linkable at low temperature intended to connect all of the components to the preform and give the sleeve its final form.

Figure 3:
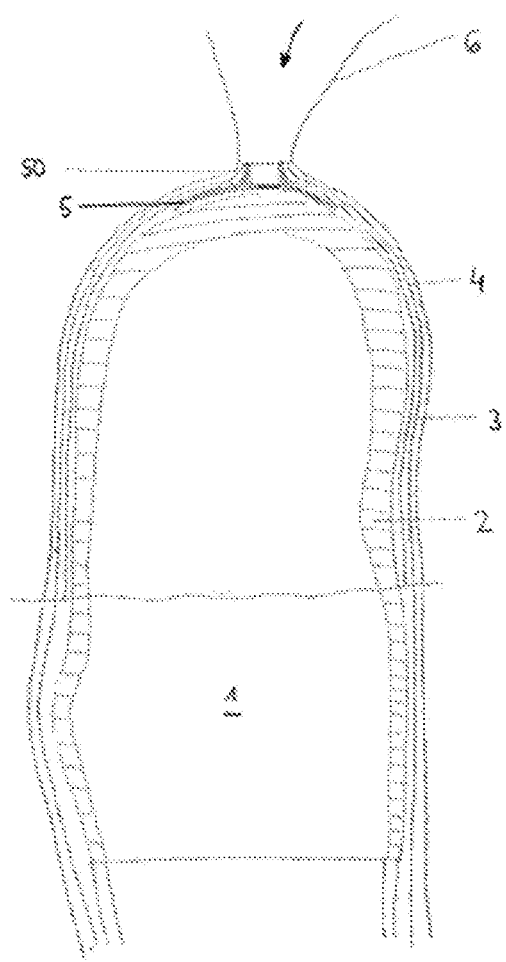
FIG. 3 is a view of the preform surrounded by the vacuum cover.

FIG. 3 thus shows, by way of example, the preform 2 on the mold 1 with a layer 3 of an elongation-preventing fabric and a polyamide discharge sheath 4, as well as a distal cup 5 comprising a threaded end 50, surrounded by a vacuum cover 6. The injection of the polymer is shown diagrammatically by the arrow.

The pressure reduction applied in the vacuum cover is typically in the order of 0 to minus 1013 hPa in relation to atmospheric pressure, which is here deemed to be equal to 1013 hPa. The application of this pressure reduction has the effect of flattening the walls of the cover against the preform, the discharge layer serving to hold the components while allowing the interstitial air to escape.

The polymer injected into the vacuum cover is advantageously made of silicone or another polymer cross-linkable at room temperature. Such a silicone is usually referred to as Room Temperature Vulcanized (RTV). This silicone is formed by a mixture of two components, in the presence of a catalyst, which ideally cross-links at a temperature of between 20 and 25° C. This silicone must be compatible with the material of the preform, that is to say have good qualities of adhesion to the preform, in order to ensure the cohesion of the stump.

The thickness of the silicone deposited around the preform is preferably in the order of 0.1 to 1 mm, but can be thicker depending on the elements placed on the preform. The vacuum cover ensures the uniformity of the layer of silicone deposited around the preform. Thus the quality of the final sleeve is not dependent on the skill of the technician.

The necessary cross-linking time is in the order of 5 to 60 minutes, but can vary significantly depending on the polymers used.

Thus, no heating is required in order to form the sleeve.

However, it may be advantageous to use an oven to accelerate the cross-linking process. Moreover, curing of the silicones is strongly advised.

Once the polymer has cross-linked, the technician will remove the vacuum cover and, if necessary, finish off the sleeve.

Figure 4:
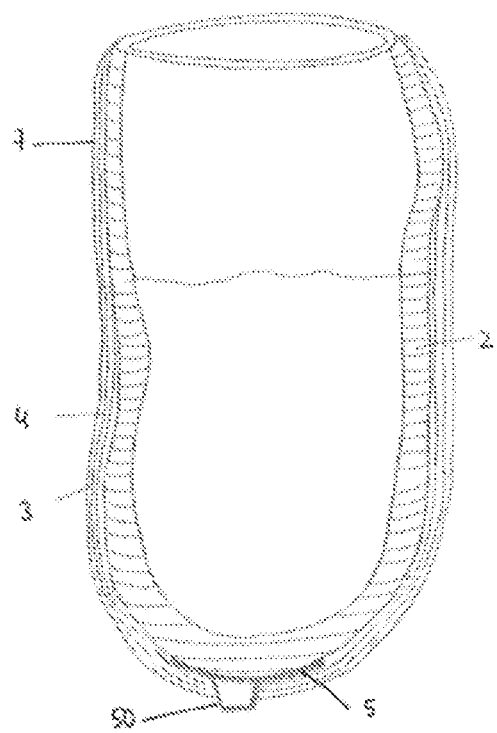
FIGS. 4 and 5 show two different embodiments of a finished sleeve.
Figure 5:
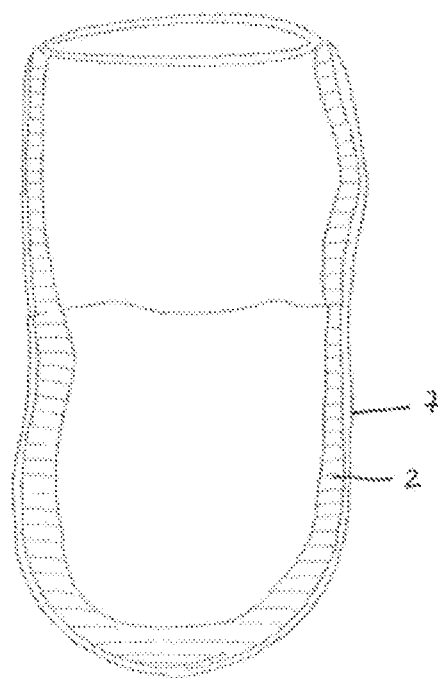

This finishing off may consist in gluing on an elasthane-based fabric (shown by reference numeral 7 in FIGS. 4 and 5, which represent two versions of a finished sleeve) and/or in applying a slippery paint. In the absence of such a covering to encourage sliding, talcum powder could be applied to the sleeve to encourage the silicone to slide on itself when positioning the sleeve onto the limb to be fitted up.

The method according to the present disclosure thus makes it possible to manufacture a sleeve specific to the wearer of the prosthesis quickly and cheaply and with repeatable quality.

REFERENCES

FR 2 799 953
FR 2 994 079

The invention claimed is:

1. A method for manufacturing a customized sleeve for a prosthesis, comprising the following steps:
    (a) providing a mold of an end of a limb of an individual who is intended to receive the prosthesis;
    (b) providing a preform made of an elastomer material, the preform comprising an open proximal end and a closed distal end;
    (c) positioning the preform on the mold;
    (d) positioning on the preform at least one element selected from among: a polymer reinforcement, a layer of an elongation-preventing fabric, a distal cup and an air discharge sheath;
    (e) positioning a vacuum cover around the preform; and
    (f) creating a vacuum and injecting a polymer cross-linkable at room temperature into the vacuum cover so as to form a coating having a uniform thickness over the preform and each element positioned on the preform.

2. The method of claim 1, wherein the preform is made of silicone gel.

3. The method of claim 2, wherein the material injected around the preform comprises a bi-component silicone.

4. The method of claim 3, wherein all of the steps are performed at a temperature of between 20 and 25° C.

5. The method of claim 4, wherein the preform has a variable thickness.

6. The method of claim 5, wherein the preform has a greater thickness at its distal end than at its proximal end.

7. The method of claim 6, further comprising, after cross-linking of the polymer injected around the preform, gluing a resilient fabric or applying a slippery paint onto an external surface of the sleeve.

8. The method of claim 1, wherein the material injected around the preform comprises a bi-component silicone.

9. The method of claim 1, wherein all of the steps are performed at a temperature of between 20 and 25° C.

10. The method of claim 1, wherein the preform has a variable thickness.

11. The method of claim 10, wherein the preform has a greater thickness at its distal end than at its proximal end.

12. The method of claim 1, further comprising, after cross-linking of the polymer injected around the preform, gluing a resilient fabric or applying a slippery paint onto an external surface of the sleeve.

* * * * *